United States Patent [19]

Moimas et al.

[11] Patent Number: 5,136,056
[45] Date of Patent: Aug. 4, 1992

[54] ZERANOL PRODUCTION

[75] Inventors: Flavio Moimas, Gorizia; Giuliano Clauti, Udine, both of Italy

[73] Assignee: C.R.C. Compagnia di Ricerca Chimici S.p.A., Udine, Italy

[21] Appl. No.: 614,371

[22] Filed: Nov. 16, 1990

Related U.S. Application Data

[63] Continuation-in-part of Ser. No. 320,942, Mar. 9, 1989, abandoned.

[51] Int. Cl.$^5$ .......................................... C07D 315/00
[52] U.S. Cl. ............................................... 549/270
[58] Field of Search ..................................... 549/270

[56] References Cited

U.S. PATENT DOCUMENTS 3,839,364 10/1974 Young ........................... 549/270

FOREIGN PATENT DOCUMENTS 0248916 12/1987 European Pat. Off. ............ 549/270
2571372 4/1986 France .............................. 549/270

OTHER PUBLICATIONS

Hidy et al., Adv. Appl. Microbiol, 22 (1977), pp. 59-82.
Pavia et al., "Organic Laboratory Techniques", 2nd ed. pp. 481-484, Saunders College Publishing, 1982.

Primary Examiner—C. Warren Ivy
Assistant Examiner—Ba K. Trinh
Attorney, Agent, or Firm—Edward S. Irons

[57] ABSTRACT

A process for producing high purity α-zeranol from a zeralenone containing surface fermentation product is described. One feature of the process entails fractional crystallization from an aqueous acetonitrile solvent of high purity α-zeranol from a solution containing a mixture of 50 to 60 parts by weight α-zeranol and 40 to 50 parts by weight β-zeranol.

19 Claims, 1 Drawing Sheet

ZERANOL PRODUCTION

This application is a continuation-in-part of application Ser. No. 07/320,942 filed Mar. 9, 1989, now abandoned, which is incorporated herein by reference.

FIELD OF THE INVENTION

This invention relates generally to the production of a high purity α-zeranol product from zeralenone.

BACKGROUND OF THE INVENTION

Compounds having the following structural formulae are hereinafter identified by the ensuing chemical names or formula numbers.

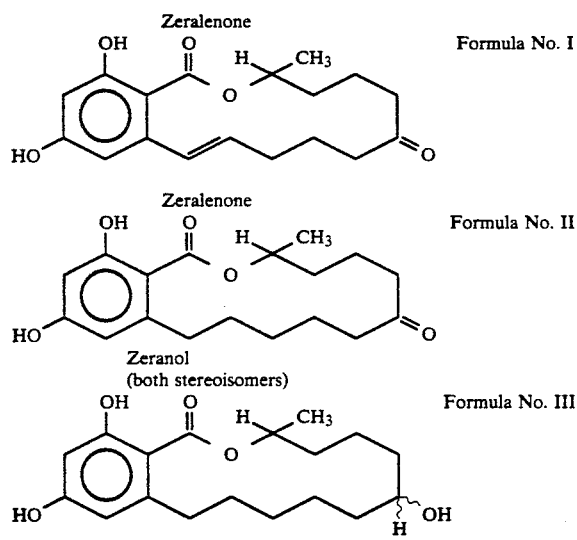

The higher melting zeranol isomer is denominated "αzeranol" and assigned Formula No. III.A; the lower melting isomer is denominated "βzeranol" and is assigned Formula No. III.B.

α and β zeranol are useful anabolic and estrogenic substances for oral and parental administration to animals. See, e.g., U.S. Pat. Nos. 3,239,345 and 4,069,339. The pharmacology of α and β zeranol and some derivatives thereof is discussed in Hidy, et al., *Advances in Applied Microbiology* 22:59-82 (1977).

Known methods for the production of α and β zeranol entail surface, see—e.g., U.S. Pat. No. 3,239,345—or submerged—see e.g., U.S. Pat. No. 3,661,712—fermentation to yield a zeralenone (Formula I) metabolite. Zeralenone recovered from the fermentation product is hydrogenated to provide a mixture of the α and β zeranol diastereomers. The diastereomers may be separated by fractional crystallization from isopropanol, see, e.g., U.S. Pat. No. 2,239,345, by esterification followed fractional crystallization, see, e.g., U.S. Pat. No. 3,687,912 or by liquid chromatography as described in EPO patent publication 0 248 916 and French Pat. No. 2,571,372. Mixtures of α and β zeranol rich in the β isomer may be recovered from the fractional crystallization mother liquor and dehydrogenated to provide a mixture of zeralanone, α-zeranol and β zeranol which is recycled for hydrogenation concurrently with the zeralenone fermentation product, see, U.S. Pat. No. 3,960,898.

SUMMARY OF THE INVENTION

This invention provides an integrated, multistep fermentation process for the efficient production of high purity α-zeranol.

Zeralenone recovered from the fermentation product is hydrogenated to provide an initial α and β zeranol mixture which may contain at least 50 weight percent of α zeranol. A unique fractional crystallization technique from aqueous acetonitrile enriches the α zeranol content of the initial mixture. This technique may be utilized in a single step or in iterated steps as appropriate to yield an α zeranol product containing not more than about 1.5 to 2 weight percent of β zeranol.

A mixture of the diastereoisomers rich in β zeranol present in the fractional crystallization mother liquors is dehydrogenated under controlled conditions, in the presence of Raney nickel and n-butyl acetate to provide zeralanone and a mixture of α and β zeranol rich in the α isomer uniquely appropriate for cycling to the zeralenone hydrogenation step.

DEFINITION

Figure 1:
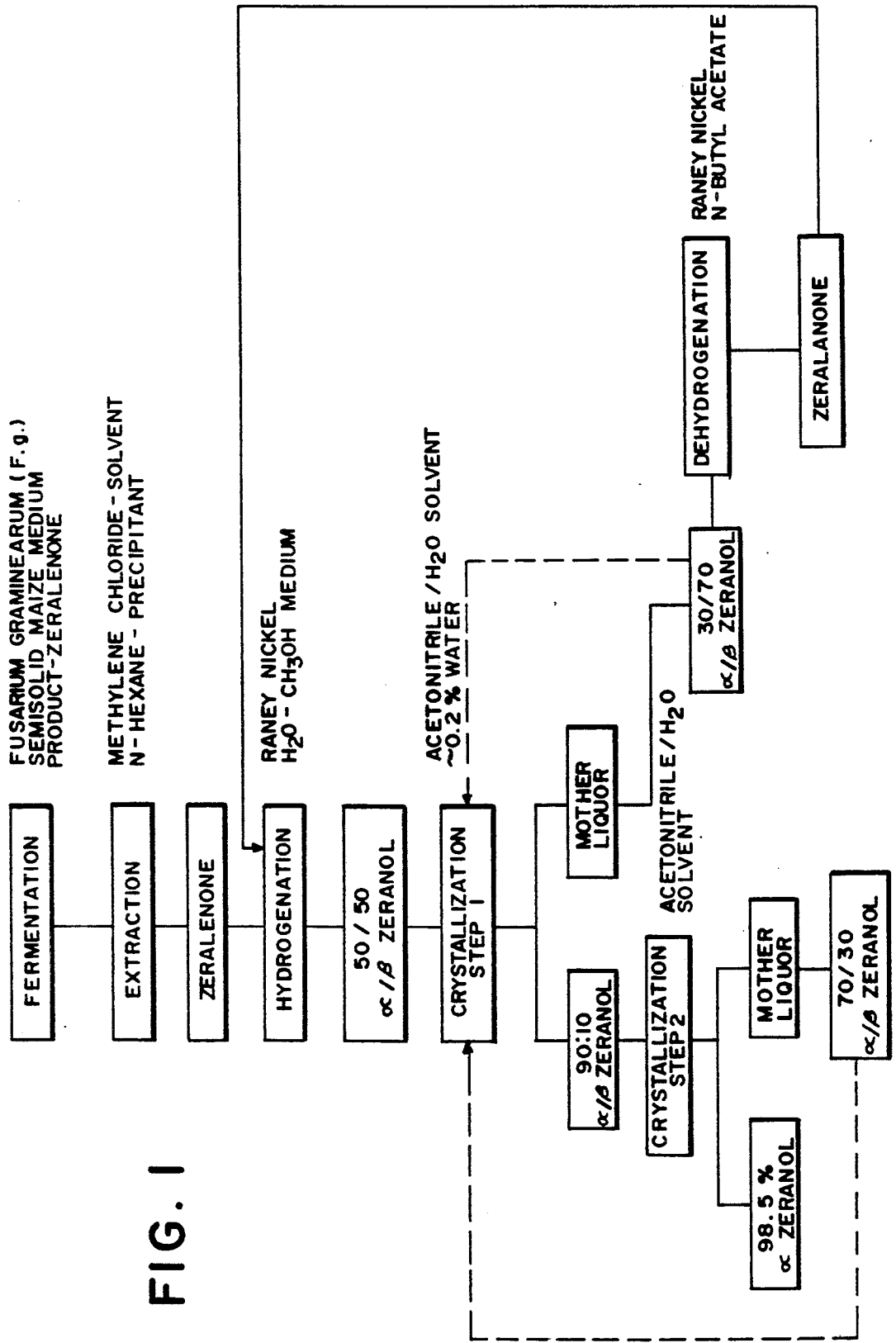
FIG. 1 is a block diagram flow sheet that generally depicts several steps included in the multistep process of the invention. Some preferred reagents and conditions are set forth on the Figure.

"Purity" or "Titre" of α-Zeranol—As used herein, the terms "purity" and "titre" of α-zeranol are synonymous. These terms refer to the percent by weight of α-zeranol in a mixture including α and β zeranol as determined by HPLC, using a Nucleosil C18 column, 4.6 mm×200 mm; eluent; acetonitrile/methanol/water 41:14:45, adjusted to pH 3.5 with phosphoric acid; retention times: α-zeranol 6.28 min., β-zeranol 5.06 min.; developer UV-VIS, λ=265 nm.

"Dilution" — As used herein, the term "dilution" means solute: solvent ratio.

GENERAL DESCRIPTION OF THE INVENTION

The several steps in this process which comprises the invention are, in part, described by reference to FIG. 1.

1. Fermentation Microorganisms

The microorganism preferred for use in the invention is *Fusarium graminearum* (F.g.), in particular a known strain of F.g. which provides an average zeralenone yield of 8 gr/kg of fermentation material.

Such a strain, transplanted on a mycologic agar slant, initially presents a superficial white aerial hyphoid development. Later the colonies become light gray and the hyphoid development disappears or turns to a pink to brownish color corresponding to the central nuclei of the colonies. The agar tends to turn brown in the area of the former aerial hyphoid development.

Strains isolated for production may be preserved in the form of a slant in a suitable medium. Production strains may be periodically revitalized on fresh agar.

Production strains are expanded in sequential prevegation and laboratory phases to provide an inoculum for the production of zeralenone. In the prevegation phase, a small amount of sterilized normal saline is applied to slants of the selected strain. The product is removed with a sterilized loop to provide a growth suspension with which glass flasks containing sterilized vegative media are inoculated. The inoculated flasks are incubated at about 24°–25° C. for about 72 hours on a rotation shaker at 150 r.p.m. This procedure may be repeated for the number of times and to the extent appropriate to provide ample inoculum for zeralenone fermentation.

2. Fermentation

A zeralenone containing metabolite is produced from the surface fermentation of F.g. on a maize substrate. Any surface fermentation device or technique may be utilized in conjunction with any appropriate substrate. The fermentation preferably takes place in glass jars which may contain, for example, about 400 grams of ground maize. The fermentation vessels are inoculated with the aforesaid inoculum diluted with sterilized normal saline. Preferably the inoculation is accomplished with a volumetric peristalic pump. The inoculated jars are incubated for from about 20 to about 30 days, preferably from about 24 to 28 days at a temperature of from about 18° C. to about 30° C., preferably from about 21° C. to about 23° C. Conventional fermentation media may be utilized. A preferred medium includes Pridham broth (malt extract 10 gr/l; yeast extract 4 gr/l; glucose 4 gr/l) and Bennet's broth, (yeast extract 1 gr/l; beef extract 1 gr/l; casitone 2 gr/l; glucose 10 gr/l).

3. Extraction

As FIG. 1 shows, the fermentation product is recovered from the glass jars and subjected to cold extraction with methylene chloride to procure a solution of the active ingredient, zeralenone. Methylene chloride is used because it is a non-solvent or poor solvent for various undesired fermentation products. Other similarly functioning non-solvents or poor solvents may be used.

The methylene chloride solution is concentrated to an oily consistency preferably by evaporation at a temperature of about 65°-70° C. and at atmospheric pressure. Zeralenone is precipitated from the oily concentrate by the addition of n-hexane and then recovered as a microcrystalline powder. Other precipitants may be used, for example, other n-hydrocarbons having less than about 10 carbon atoms and non-polar solvents such as toluene and cyclohexane.

The resulting slurry is filtered and the recovered solid zeralenone is dried, preferably by air circulation, after having been laid out on trays. Air circulation is appropriately conducted at a temperature of from about 60° C. to about 70° C. for a time period of from about 12 to about 30, preferably from about 16 to about 24 hours.

The mother liquor (hexane filtrate) is purified by distillation and recycled.

4. Hydrogenation of Zeralenone

As FIG. 1 shows, the zeralenone product of the extraction step is hydrogenated to produce a mixture of α-zeranol and β-zeranol. Procedures for the hydrogenation of zeralenone are known. See, e.g., U.S. Pat. No. 3,239,345. Any procedure effective to yield the desired mixed α and β zeranol product may be used. Hydrogenation pressure at a temperature of from about 40° C. to 50° C. under 2 to 4 atmospheres in the presence of Raney nickel in a water methanol medium is preferred. The initial hydrogenation reaction product is a methyl alcohol solution of an α and β zeranol mixture.

The methyl alcohol is evaporated under agitation to provide a concentrated solution which is then cooled to precipitate a mixture of solid α and β zeranol typically containing about 50% to 60% by weight α-zeranol. The precipitate is placed on trays and air dried at about 60° C. to 70° C. for about 20-25 hours.

5. Recovery of High Purity α-zeranol

High purity α-zeranol is derived from the hydrogenation product mixture of α and β zeranol by fractional crystallization from a solvent consisting essentially of 90 to 99.88 acetonitrile and 10% to about 0.02% by volume of water, preferably from about 98 to about 99.8% acetonitrile and from about 2 to about 0.2% by volume of water. Preferably the ratio of said mixture to said solvent is from about 1:15 to about 1:30. The solution is cooled from an elevated temperature, preferably about the reflux temperature thereof to from about 15° C. to about 35° C. at a rate of from about 5° C. to about 10° C. per hour. Cooling results in the precipitation of a crystallized product mixture enriched, typically about 20% by weight in α-zeranol. Typically a single fractional crystallization yields a product containing about 70% to about 75% in weight of the α-zeranol present in the initial α and β zeranol mixture and a mother liquor enriched in β-zeranol.

As shown by FIG. 1, for example, the mother liquor from a first crystallization step may contain from about 25/75 to about 40/60 percent by weight, typically a 30/70 percent by weight, mixture of α and β zeranol. The first crystallization step product which typically contains about 90% by weight α-zeranol, may be subjected to one or more additional crystallization steps under like conditions to yield a final mixture containing at least about 98, normally 98.5%, by weight of α-zeranol, and a second mother liquor which may contain a mixture of α and β zeranol in a weight ratio of from about 60/40 to about 75/25, typically 70/30, α/β zeranol.

In the preferred practice of the invention, a product containing at least about 98 to 98.5 weight percent α-zeranol is obtained in two fractional crystallization steps as shown by FIG. 1. For that purpose a 90% by weight α-zeranol product should be obtained from the first step. The first step may be iterated as many times as may be appropriate to provide an α-zeranol product of the desired, e.g., 98.5% purity.

6. Recycle of α/β Zeranol Mixtures Recovered from First and Subsequent Crystallization Step Mother Liquors α and β zeranol mixtures are recovered by crystallization from the mother liquors which result from the first and subsequent crystallization steps conducted to produce a final α-zeranol product containing at least about 98 to 98.5% by weight α-zeranol. Such mixtures are combined in a ratio appropriate to provide a resultant mixture containing at least about 50% by weight α-zeranol for recycling to a first crystallization step, e.g., crystallization step 1 as shown by FIG. 1.

Referring specifically to FIG. 1 for purposes of illustration, equal quantities of a mixture containing α and β zeranol in a 30/70 weight ratio and recovered from the crystallization step/mother liquor and of a mixture containing α and β zeranol in a 70/30 weight ratio recovered from step 2 mother liquor are combined and recycled to the first crystallization step.

7. Dehydrogenation of α/β Zeranol Content of Crystallization Mother Liquor

The mother liquors from a first or subsequent fractional crystallization steps may contain a mixture of α and β zeranol which is rich in β zeranol.

Such β zeranol rich mixtures are partially dehydrogenated by Raney nickel in n-butyl acetate at reflux or boiling temperature of about 126° C. The dehydrogenation process is terminated at about 70% to about 90%, preferably about 80% to 85% conversion to provide a dehydrogenation reaction product mixture containing about 80-85 weight percent of zeralanone and about 15 to 20 weight percent of a mixture of α and β zeranol of which about 75 to 80 weight percent is α zeranol.

The use of n-butyl acetate permits the dehydrogenation reaction to proceed at atmospheric pressure. Any need for operation under pressure in an oxygen free environment is avoided. Highly purified zeralanone enriched in α-zeranol is produced.

The dehydrogenation reaction mixture is cooled to from about 50° C. to about 55° C. at which temperature the Raney nickel catalyst is removed. By so proceeding, precipitation of the dehydrogenation reaction product mixture is avoided and colored impurities typically formed during the dehydrogenation of phenol substances such as α and β zeranol are eliminated. The dehydrogenated mixture is concentrated and the product mixture is further cooled to from about 10° C. to about 20° C., preferably about 15° C. The cooling step yields a crystalline mixture comprising zeralanone, α-zeranol and β-zeranol substantially free chemical impurities. The mixture of α and β zeranol typically contains from about 75% to 85%, preferably about 80% by weight α-zeranol.

As shown by FIG. 1, this crystalline mixture is appropriately recycled to zeralenone hydrogenation step.

In the following Table 1 the results of crystallization tests carried out with different acetonitrile/water ratios are reported.

TABLE 1

Titre (purity) and yield changes of α zeranol crystallized from acetonitrile/water (final temperature 30° C.)

| Test | α:β Zeranol Mixture | CH$_3$CN—H$_2$O | Dilution g/ml | α zeranol titre % HPLC | Weight Yield | α zeranol yield (%) |
|---|---|---|---|---|---|---|
| 1 | 58:42 | 10:5 | 1:10 | 92.0 | 24.3 | 38.5 |
| 2 | 58:42 | 10:1 | 1:10 | 93.0 | 25.5 | 40.9 |
| 3 | 58:42 | 9.9:0.1 | 1:20 | 92.0 | 39.0 | 61.9 |
| 4 | 58:42 | 10:0 | 1:22 | 83.5 | 47.2 | 67.9 |
| 5 | 54:46 | 10:1 | 1:10 | 91.0 | 21.6 | 36.4 |
| 6 | 54:46 | 9.95:0.01 | 1:22 | 92.8 | 42.3 | 72.7 |
| 7 | 54:46 | 9.98:0.02 | 1:20 | 91.6 | 40.8 | 69.2 |
| 8 | 54:46 | 9.98:0.02 | 1:22 | 92.0 | 43.1 | 73.4 |

The following Table 2 shows how the final temperature and the solute/solvent ratio effect yield and diastereoselectivity. Best results are obtained for ratios ranging from 1:20 to 1:22, whereas when the final temperature falls, yield increases to the detriment of selectivity.

TABLE 2

α-zeranol titre and yield changes as functions of dilution (solute:solvent ratio) and final temperature (solvent:acetonitrile/water 99.8:0.2; starting mixture α:β zeranol = 54:46)

| Test | Dilution | α-Zeranol Titre (% HPLC) | Final Temperature (°C.) | Weight Yield (%) | α-Zeranol Yield (%) |
|---|---|---|---|---|---|
| 1 | 1:20 | 68.6 | 15 | 53.0 | 67.3 |
| 2 | 1:20 | 73.0 | 20 | 52.6 | 71.1 |
| 3 | 1:20 | 89.0 | 27 | 43.0 | 70.9 |
| 4 | 1:20 | 90.8 | 30 | 39.5 | 65.8 |
| 5 | 1:22 | 92.0 | 25 | 40.3 | 62.7 |
| 6 | 1:22 | 94.0 | 30 | 42.4 | 73.8 |
| 7 | 1:25 | 86.0 | 20 | 39.7 | 63.2 |
| 8 | 1:25 | 91.7 | 25 | 35.0 | 59.4 |
| 9 | 1:25 | 93.7 | 30 | 32.8 | 56.9 |

EXAMPLE 1

Separation of α-zeranol from the α, β zeranol mixture 4.5 g of an α, β zeranol mixture (50:50) were placed in acetonitrile containing about 1% water (100 ml) and active charcoal (0.1 g) was added. The mixture was refluxed for 15 min., then the warm solution was filtered on Celite; the filtrate was heated to obtain a clear solution, that is to about 80° C. The solution was cooled under stirring, adjusting the fall in temperature to about 6°-7° C./hour, thereby the solution temperature after about 8 hours being 30° C. The precipitate was filtered, washed with 10 ml of cold acetonitrile, finally dried. 1.8 g (40%) of α-zeranol was obtained, with 91% purity.

The whole amount of α-zeranol (1.8 g) was dissolved in 55 ml of acetonitrile/water (99.5:0.5); heating to reflux, then filtered on Celite and the filtrate was heated to 80° C. The clear solution was cooled adjusting the fall in temperature to about 6°-7° C./hour; during about 8 hours the solution was cooled to 30° C., under stirring. The solid was filtered and washed with 5 ml of cold acetonitrile; after drying 1.26 g of α-zeranol was obtained, with a 98.5% diastereomeric purity.

Titre was determined by analytic HPLC, as described above; m.p. 180°-182° C.; [α]D$^{20}$=+46.2 (c=1.0; methanol).

EXAMPLE 2

Separation of α-zeranol from the α, β-zeranol mixture 3.59 kg of an α, β-zeranol mixture (55:45), acetonitrile with 0.5% water (80 l) and active charcoal (0.05 kg) were placed into a 150 l crystallizer. The mixture was refluxed for 30 min., warm filtered and the filtrate was refluxed again. The obtained clear solution was cooled adjusting the fall in temperature to about 8°-10° C./hour, under strong mechanic stirring, so as to obtain a controlled crystallization. Crystal withdrawals were carried out at 42° C., 36° C. and 30° C. on which crystals HPLC analysis was effected a described in Example 1: content in α-zeranol proved to be extremely constant (91.9%, 92.3% and 91.8%, respectively, at the above cited temperatures). Stirring was continued overnight and for 12 hours more at 30° C.; then the product was filtered and dried to obtain 1.40 kg (38.99%) of an α-zeranol with a 93.5% titre. This product was dissolved in 42 l of acetonitrile with 1% of water and crystallized following the same procedure as above. 1.01 kg of final product was obtained, with a 98.6% titre (HPLC), m.p.=181°-182° C., $[\alpha]D^{20}=46.2$ (c=1.0; methanol).

EXAMPLE 3

Recycle of the α, β-zeranol mixture (α-zeranol titre about 30%) via oxidation

Mother liquors from the first crystallization described in Example 2 (80 l) were concentrated to small volume (about 10 l). The suspension was filtered to give 1.92 kg of an α, β-zeranol mixture with an α-zeranol titre of 29.2% (determined via HPLC, as in Example 1). This product was oxidized with Raney nickel (2.5 kg) in n-butyl acetate (30 l). After refluxing for 6 hours, HPLC shows a content of zeralanone of about 80%, an α-zeranol content of about 12–14% and a β-zeranol content of 6–8%. (For quantitative determination, a Bio-sil ODS-5S column, 4 mm×150 mm was used; eluent as in Example 1; retention times: zeralanone=5.04 min., α-zeranol=3.51 min., β-zeranol=2.63 min.). The catalyst was filtered off and washed with 10 l of n-butyl acetate; then the solution was evaporated to 5 l, obtaining 1.6 kg of a mixture of α and β-zeranol and zeralanone, as above described. Said mixture was hydrogenated together with zeralenone from Fusarium fermentation, to give an α, β-zeranol mixture with α-zeranol titre from 60 to 65%.

EXAMPLE 4

Recycle of the α, β-zeranol mixture (α-zeranol titre about 30%) via crystallization Mother liquors from the first crystallization described in Example 2 (80 l) were concentrated to small volume, then the precipitate consisting of the α, β-zeranol mixture (1.92 kg) with an α-zeranol titre of 29.2%, was filtered.

This mixture was admixed with an α, β-zeranol mixture (4.36 kg, α-zeranol titre 71%), obtained from mother liquors from the second crystallization. The final mixture (6.28 kg) contained α-zeranol in a 58.2% percentage. This mixture was crystallized with the α, β-zeranol mixture from catalytic reduction of Zeralenone, as described in Example 2.

We claim:
1. The process which consists essentially of:
    (i) dissolving a first mixture of α and β zeranol containing at least about 50% by weight α-zeranol said first mixture having been produced by the hydrogenation of zeralenone in a solvent consisting essentially of aqueous acetonitrile containing from about 0.02% to about 10% by volume of water to provide a first solution containing from about 10 to about 30 parts by weight of said solvent per part by weight of said first mixture;
    (ii) cooling said first solution from an elevated temperature of at least about 80° C. to a final temperature of at least about 40° C.,
    said cooling being effected at a controlled rate of from about 5° C. to about 10° C. per hour
    to provide a first mother liquor and, as a precipitate, a second mixture of α and β zeranol, the α-zeranol content being greater than the α-zeranol content of said initial mixture;
    (iii) separating said second mixture of α zeranol and β zeranol from said first mother liquor.
2. A process as defined by claim 1 in which said aqueous acetonitrile solvent contains from about 0.2% to about 2% by volume of water.
3. A process as defined by claim 1 in which the α-zeranol content of said second mixture is at least about 20% by weight greater than the α-zeranol content of said first mixture.
4. A process as defined by claim 2 in which said first solution contains from about 20 to about 22 parts by weight of said solvent per part by weight of said first mixture.
5. A process as defined by claim 2 in which said elevated temperature from which said solution is cooled in step (iii) is the reflux temperature of said solution.
6. A process as defined by claim 2 in which said elevated temperature from which said solution is cooled in step (iii) is the reflux temperature of said solution and said solution is cooled to a final temperature of from about 15° C. to about 35° C.
7. A process as defined by claim 1 further comprising:
    (iv) dissolving said second mixture of α and β zeranol in a solvent consisting essentially of aqueous acetonitrile containing from about 0.02% to about 10% by volume of water to provide a second solution;
    (v) cooling said second solution from an elevated temperature of at least about 80° C. to a final temperature of at least about 40° C.
    said cooling being effected at a controlled rate of from about 5° C. to about 10° C. per hour
    to provide a second mother liquor and a third mixture of α and β zeranol, the α-zeranol content of said third mixture being greater than the α-zeranol content of said second mixture; and
    (vi) separating said third mixture of α and β zeranol from said second mother liquor.
8. A fractional crystallization process for separating a product containing at least about 90% by weight α-zeranol and not more than about 10% by weight β-zeranol from a first mixture of α and β-zeranol containing from about 50% to about 60% by weight α-zeranol said process consisting essentially of
    (i) dissolving said first mixture in a solvent consisting essentially of aqueous acetonitrile containing from about 0.2% to about 2% by volume of water to provide a first solution containing from about 10 to about 30 parts by weight of said solvent per part by weight of said first mixture;
    (ii) cooling said first solution from the reflux temperature thereof to a final temperature of at least from about 15° C. to about 35° C.
    said cooling being effected at a controlled rate of from about 5° C. to about 10° C. per hour.
    to provide a first mother liquor enriched in β zeranol and as a precipitate, a second, crystallized product mixture of α and β zeranol containing at least about 70% by weight of the α zeranol present in said first mixture, said α-zeranol having a purity of at least about 90%;

(iii) separating said second crystallized product mixture of α and β-zeranol from said first mother liquor enriched in β-zeranol.

9. A process a defined by claim 8 in which said first solution contains from about 20 to about 22 parts by weight of said solvent per part by weight of said first mixture.

10. A process as defined by claim 8 or claim 9 in which said first mixture is produced by the hydrogenation of zeralenone, zeralanone or a mixture thereof.

11. A process as defined by claim 8 further comprising
   (iv) cooling said first mother liquor, after concentration, from an elevated temperature to provide a second mother liquor and a third mixture of α and β zeranol
      said third mixture containing from about 30% by weight to about 40% by weight α-zeranol;
   (v) subjecting said second crystallized product to fractional crystallization to provide a third mother liquor and a fourth mixture of α and β zeranol containing from about 60 to about 75% by weight α-zeranol;
   (vi) combining said third mixture and said fourth mixture of α and β zeranol in proportions to provide a fifth mixture of α and β zeranol containing at least about 50% by weight α-zeranol; and
   (vii) cycling said fifth mixture to step 1.

12. In a process for separating a mixture of α and β zeranol containing about 50% to 60% α-zeranol, said mixture having been produced by the hydrogenation of zeralenone, the improvement which consists of:
   (i) providing a solution of said mixture of α zeranol and β zeranol containing about 50% to 60% α-zeranol in a solvent consisting of acetonitrile containing 0.2 to 2% of water, the ratio of said initial mixture to said solvent being from about 1:15 to 1:30;
   (ii) cooling said solution at a rate of about 5° C. to 10° C. per hour from the reflux temperature thereof to a final temperature of 15° C. to 35° C. to provide a crystallized product mixture containing 70% to 75% of the α-zeranol present in said initial mixture; said α-zeranol having a purity higher than 90%; and a mother liquor enriched in β-zeranol; and
   (iii) separating said crystallized product mixture from said mother liquor.

13. A fractional crystallization process for separating a product containing at least about 98% by weight of α-zeranol and not more than about 2% by weight of β-zeranol from a first mixture of α and β zeranol containing about 50% to about 60% by weight of α-zeranol, said process consisting essentially of
   (i) dissolving said first mixture in a solvent consisting essentially of aqueous acetonitrile containing from about 0.2% to about 2% by volume of water to provide a first solution containing from about 10 to about 30 parts by weight of said solvent per part by weight of said first mixture;
   (ii) cooling said first solution from the reflux temperature thereof to a final temperature of at least from about 15° C. to about 35° C.
      said cooling being effected at a controlled rate of from about 5° C. to about 10° C. per hour
      to provide a first mother liquor enriched in β zeranol and, as a precipitate, a second, crystallized produced mixture of α and β zeranol containing at least about 70% by weight of α zeranol present in said first mixture, said α-zeranol having a purity of at least about 90%;
   (iii) separating said second crystallized product mixture of α and β zeranol from said first mother liquor enriched in β-zeranol.
   (iv) dissolving said second product mixture in a solvent consisting essentially of aqueous acetonitrile containing from about 0.02% to about 2% by volume of water to provide a second solution containing from about 25 to about 35 parts by weight of said solvent per part by weight of said second mixture;
   (v) cooling said second solution from the reflux temperature thereof to a final temperature of from about 15° C. to about 35° C.
      said cooling being effected at a rate of from about 5° C. to about 10° C. per hour
      to provide a second mother liquor and, as a precipitate, a third mixture of α and β zeranol
      said third mixture containing at least about 98% by weight of α-zeranol and not more than about 2% by weight of β zeranol, and
   (vi) separating said third mixture from said second mother liquor.

14. A process as defined by claim 13 in which said first mixture of α and β zeranol is produced by hydrogenating zeralenone, zeralanone or a mixture thereof.

15. A process as defined by claim 13 further comprising:
   (vii) cooling said first mother liquor from an elevated temperature, after concentration, to provide a second mother liquor and a third mixture of α and β zeranol
      said third mixture containing from about 30% by weight to about 40% by weight α-zeranol;
   (viii) dehydrogenating at least a portion of said third mixture to produce a product mixture comprising zeralenone, α-zeranol and β zeranol; and
   (ix) hydrogenating said dehydrogenation product mixture to produce a mixture of α and β zeranol containing at least about 50% by weight α zeranol.

16. A process as defined by claim 13 further comprising separation of mixtures of α and β zeranol from each of said first and second mother liquors, and utilizing one or both of said separated mixtures as at least a portion of said first mixture of α and β zeranol.

17. A process as defined by claim 1 in which said first solution contains from about 20 to about 22 parts by weight of said solvent per part by weight of said first mixture.

18. A process as defined by claim 1 in which said elevated temperature from which said solution is cooled in step (iii) is the reflux temperature of said solution.

19. A process as defined by claim 1 in which said elevated temperature from which said solution is cooled in step (iii) is the reflux temperature of said solution and said solution is cooled to a final temperature of from about 15° C. to about 35° C.

* * * * *